(12) United States Patent
Kawase et al.

(10) Patent No.: US 10,064,592 B2
(45) Date of Patent: Sep. 4, 2018

(54) COMPUTED TOMOGRAPHIC MAMMOGRAPHY APPARATUS

(71) Applicant: CANON KABUSHIKI KAISHA, Tokyo (JP)

(72) Inventors: Junya Kawase, Yokohama (JP); Takeo Tsukamoto, Kawasaki (JP); Nobuhiro Ito, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 27 days.

(21) Appl. No.: 15/023,643

(22) PCT Filed: Nov. 11, 2014

(86) PCT No.: PCT/JP2014/005649
§ 371 (c)(1),
(2) Date: Mar. 21, 2016

(87) PCT Pub. No.: WO2015/075898
PCT Pub. Date: May 28, 2015

(65) Prior Publication Data
US 2016/0242717 A1    Aug. 25, 2016

(30) Foreign Application Priority Data
Nov. 20, 2013  (JP) .................................. 2013-239626

(51) Int. Cl.
*A61B 6/00*   (2006.01)
*A61B 6/03*   (2006.01)
(Continued)

(52) U.S. Cl.
CPC .............. *A61B 6/502* (2013.01); *A61B 6/032* (2013.01); *A61B 6/06* (2013.01); *A61B 6/107* (2013.01); *A61B 6/4435* (2013.01); *A61B 6/4476* (2013.01)

(58) Field of Classification Search
None
See application file for complete search history.

(56) References Cited

U.S. PATENT DOCUMENTS

| 6,164,820 A | 12/2000 | Hell et al. |
| 6,175,117 B1 | 1/2001 | Komardin et al. |

(Continued)

FOREIGN PATENT DOCUMENTS

| EP | 2407109 A1 | 1/2012 |
| EP | 2586375 A1 | 5/2013 |

(Continued)

OTHER PUBLICATIONS

U.S. Appl. No. 15/023,639, filed Mar. 21, 2016.

*Primary Examiner* — Hoon Song
(74) *Attorney, Agent, or Firm* — Canon USA, Inc., IP Division

(57) ABSTRACT

A mammographic CT apparatus includes: a gantry, including a front face plate having an insertion opening for inserting a breast into an accommodation portion; a radiation tube disposed within the gantry; a sensing device disposed within the gantry so as to face the radiation tube, to detect radiation which has been emitted from the radiation tube and been transmitted through the accommodation portion; a driving unit to rotate the radiation tube and the sensing device around a rotation axis set in the normal direction of the insertion opening, at the same angular speed and same direction; and a collimator configured to rotate around the rotation axis synchronously with the radiation tube and sensing device. The collimator is disposed near the accommodation portion, and an irradiation region of radiation emitted from the radiation tube is restricted such that a breast inserted to the accommodation portion is irradiated to the tip.

15 Claims, 8 Drawing Sheets

(51) Int. Cl.
*A61B 6/06* (2006.01)
*A61B 6/10* (2006.01)

(56) References Cited

U.S. PATENT DOCUMENTS

| | | |
|---|---|---|
| 6,987,831 B2 | 1/2006 | Ning |
| 2004/0234021 A1* | 11/2004 | Hoffman ................ A61B 6/032 378/4 |
| 2006/0262898 A1 | 11/2006 | Partain et al. |
| 2007/0098141 A1 | 5/2007 | Hjarn et al. |
| 2008/0049904 A1 | 2/2008 | Beyerlein et al. |
| 2009/0080604 A1 | 3/2009 | Shores et al. |
| 2011/0096897 A1 | 4/2011 | Hiromichi et al. |
| 2014/0093035 A1 | 4/2014 | Beekman |
| 2014/0119505 A1* | 5/2014 | Ohi ........................ A61B 6/037 378/37 |

FOREIGN PATENT DOCUMENTS

| | | |
|---|---|---|
| JP | 2004105729 A | 4/2004 |
| JP | 2008093135 A | 4/2008 |
| JP | 2010075338 A | 4/2010 |
| JP | 2012120651 A | 6/2012 |
| JP | 2013-22040 A | 2/2013 |
| JP | 2013-22041 A | 2/2013 |
| WO | 2008/054279 A1 | 5/2008 |

\* cited by examiner

COMPUTED TOMOGRAPHIC MAMMOGRAPHY APPARATUS

TECHNICAL FIELD

The present invention relates to a medical computed tomography (hereinafter, "CT") apparatus, and more particularly relates to a computed tomographic mammography apparatus (hereinafter, "mammographic CT apparatus" used for taking images of breasts.

BACKGROUND ART

In addition to breast cancer examinations by palpation and ultrasound diagnosis, mammographic CT apparatuses have come to be used which can display within the breast in three-dimensional (3D) images.

PTL 1 discloses CT breast imaging made up of a gantry to which a cone-beam radiation source and a sensing device are mounted. The subject lies prone on a table having a breast insertion opening, with the gantry located so as to surround the breast.

CITATION LIST

Patent Literature

PTL 1: U.S. Pat. No. 6,987,831

SUMMARY OF INVENTION

Technical Problem

In a conventional mammographic CT apparatus, the breast is inserted from the insertion opening into an accommodation portion, while the breastbone is pressed against the upper face of a top panel. The breast overlaps an X-ray irradiation area in the accommodation portion, and thus an X-ray transmission image of the breast can be taken. The X-ray irradiation region of the mammographic CT apparatus needs to be close to the top panel, so that images of the base portions of the breast toward the breastbone can also be taken. On the other hand, leakage of X-rays from the X-ray irradiation region to the subject side must be prevented.

The apparatus according to PTL 1 has a configuration where a collimator defining the X-ray irradiation region is integrally built into the X-ray generator, around the focal point. However, the collimator built into the X-ray generator is at a position away from the sensing device, so an X-ray penumbra is formed at a wide region on the outer side of the X-ray irradiation region. Accordingly, simply placing the collimator near the focal point may result in leakage of X-rays to the subject. There is also a problem that even slight positional shifting of the X-ray generator results in the X-ray irradiation region defined by the collimator greatly shifting on the sensing device.

The present invention provides a mammographic CT apparatus using radiation such as X-rays, in which both leakage of radiation to the subject side due to spreading of the radiation penumbra, and positional shift of the irradiation region on the sensing device due to positional shift of the radiation generator, are suppressed.

Solution to Problem

A mammographic CT apparatus includes: a gantry, including a front face plate in which an insertion opening is formed for inserting a breast into an accommodation portion; a radiation tube disposed within the gantry; a sensing device disposed within the gantry so as to face the radiation tube, and configured to detect radiation which has been emitted from the radiation tube and been transmitted through the accommodation portion; a driving unit configured to rotate the radiation tube and the sensing device around a rotation axis set in the normal direction of the insertion opening, at the same angular speed and same direction; and a collimator configured to rotate around the rotation axis synchronously with the radiation tube and sensing device. The collimator is disposed near the accommodation portion, and an irradiation region of radiation emitted from the radiation tube is restricted such that a breast inserted to the accommodation portion is irradiated up to the tip thereof.

Further features of the present invention will become apparent from the following description of exemplary embodiments with reference to the attached drawings.

DESCRIPTION OF EMBODIMENTS

Figure 1:
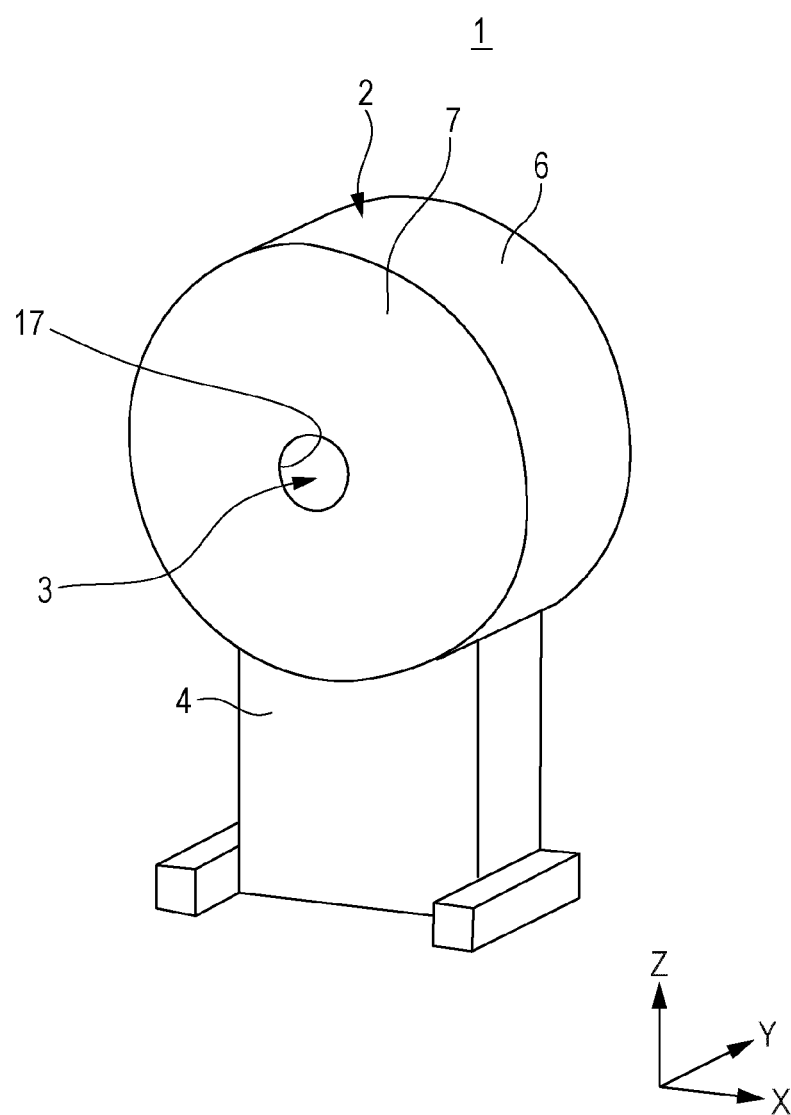
FIG. 1 is an overall perspective view of a mammographic CT apparatus according to the present invention.

Embodiments to carry out the present invention will be described with reference to the drawings. Note that in the drawings referenced below, the same reference numerals denote the same components.

First Embodiment

Overview of Mammographic CT Apparatus

Figure 2A:
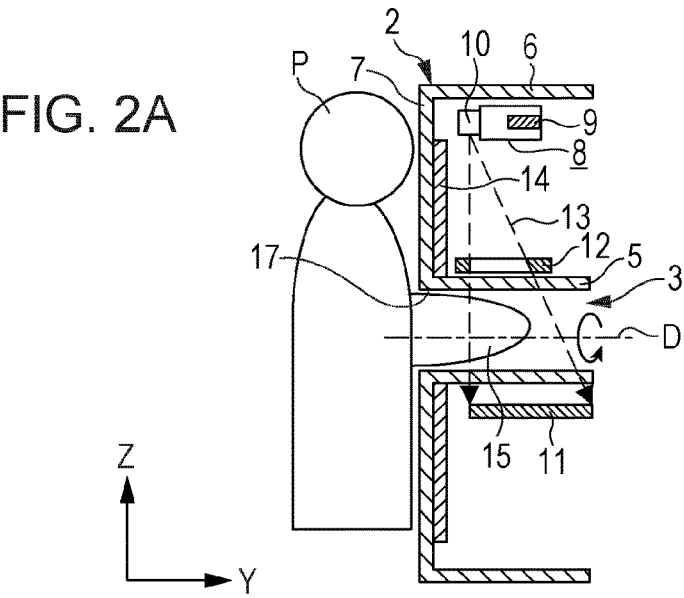
FIG. 2A is a cross-sectional view of a mammographic CT apparatus according to a first embodiment, as viewed from the X direction in FIG. 1.
Figure 2B:
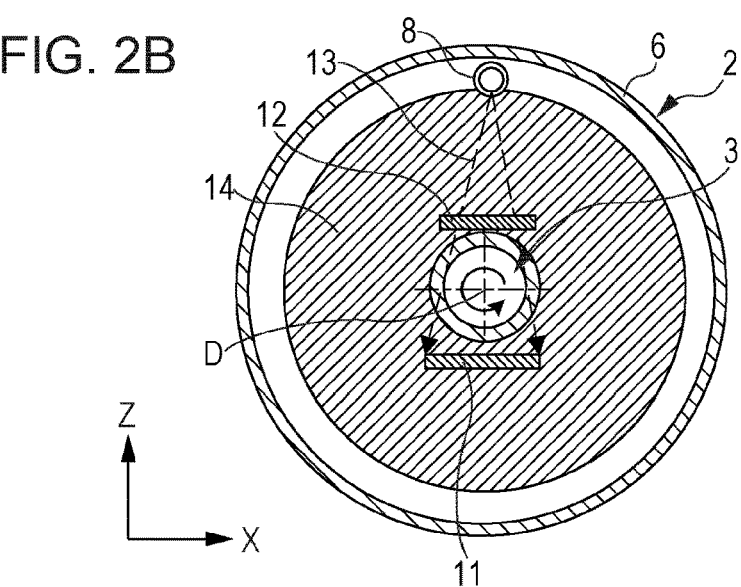
FIG. 2B is a cross-sectional view of the mammographic CT apparatus according to the first embodiment, as viewed from the Y direction in FIG. 1.
Figure 2C:
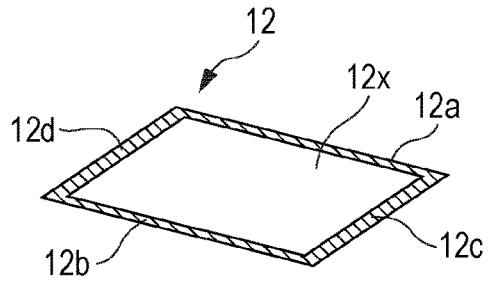
FIG. 2C is an enlarged perspective view of a collimator.
Figure 3:
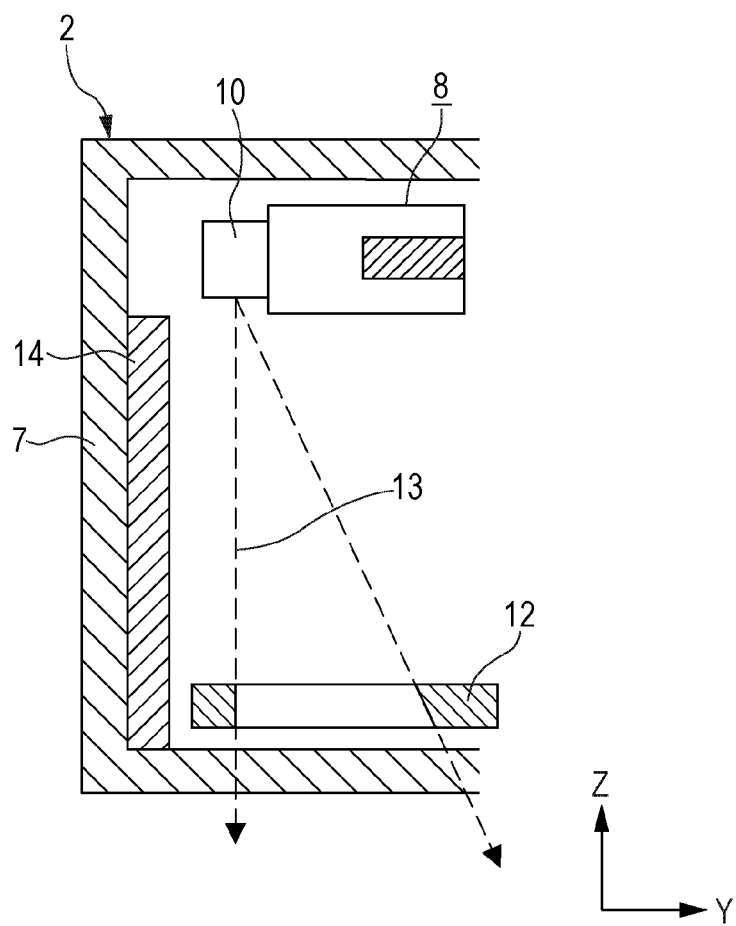
FIG. 3 is an enlarged view of around a collimator according to the first embodiment.

A mammographic CT apparatus 1 includes a gantry 2 configuring a chamber within which is stored a radiation source, a collimator 12, and so forth, as illustrated in FIGS. 1 through 3. At the center portion of the gantry 2 is provided an accommodation portion 3 into which a breast 15 of a subject P is inserted. A supporting portion 4 supports the gantry 2.

The gantry 2 is a hollow disc-shaped member, having an inner peripheral plate 5 which surrounds the accommodation portion 3, an outer peripheral plate 6 which surrounds the outer periphery, a front face plate 7 which connects the inner peripheral plate 5 and the outer peripheral plate 6 at the front side, and an unshown back plate which covers the back side. The front face plate 7 has formed therein an insertion opening 17 through which the breast 15 is inserted to the accommodation portion 3. The radiation tube 8, a sensing device 11, and a later-described collimator 12 are supported by a rotating plate (omitted from illustration) within the gantry 2, so that these three are integrally rotated by a driving unit 101 (see FIG. 4) during CT imaging. This rotation is performed on a rotational axis D established in the normal direction of the insertion opening 17. The rotational axis D passes through the inner side of the accommodation portion 3 and extends in the direction of insertion and removal of the breast 15 to and from the accommodation portion 3 (Y direction). Accordingly, the radiation tube 8, sensing device 11, and collimator 12 are rotated at the same angular speed. When imaging with the mammographic CT apparatus 1, the subject P inserts a breast 15 into the accommodation portion 3 through the insertion opening 17, from the front face side of the front face plate 7 of the gantry 2, and maintains this posture for CT imaging. Note that the front face plate 7 is erect in the present embodiment, so the subject P stands in front of the front face plate 7 for the examination. However, the mammographic CT apparatus 1 according to the present invention may be laid sideways, so that the front face plate 7 serves as the top panel of the above-described related art, with the subject P lying prone on the front face plate 7 for the examination. In this case, the inner peripheral plate 5 may be omitted.

Radiation Tube

As illustrated in FIGS. 2A through 3, the radiation tube 8 is a transmissive radiation tube, including an electron gun 9 to generate an electron beam, and an emitter 10. A heat filament type electron source, for example, can be used for the electron gun 9. The emitter 10 has a transmitting target, where a target layer that generates radiation under irradiation of the electron beam from the electron gun 9 is layered on a radiation transmitting support substrate. The material making up the support substrate is preferably one which has sufficient strength to support the target layer, absorbs little radiation generated at the target layer, and has high thermal conductivity, so that heat generated at the target layer can be quickly dissipated. Examples of such a material include diamond, silicon carbide, aluminum nitride, and so forth. The material making up the target layer preferably has a high melting point and high radiation generation efficiency. Examples of this material include tungsten, tantalum, molybdenum, alloys thereof, and so forth. The radiation tube 8 is supported by an unshown rotating plate which is rotated by the driving unit 101 (see FIG. 4), and rotates on the rotational axis D extending in the direction of insertion and removal of the breast 15 to and from the accommodation portion 3.

Sensing Device

The sensing device 11 is provided at a position facing the radiation tube 8 (emitter 10) across the accommodation portion 3, as illustrated in FIGS. 2A through 3. The sensor area of the sensing device 11 is usually a size which matches an irradiation region 13 of radiation which is defined by the later-described collimator 12. The shape of the sensor area is square, to match the shape of the irradiation region 13. The sensing device 11 is supported by the unshown rotating plate which is rotated by the driving unit 101 (see FIG. 4), along with the radiation tube 8. The sensing device 11 rotates on the rotational axis D extending in the direction of insertion and removal of the breast 15 to and from the accommodation portion 3, in the same direction and the same angular speed as the radiation tube 8, by the rotation of the rotating plate.

Collimator

The collimator 12 is disposed between the radiation tube 8 and accommodation portion 3 at a position near the accommodation portion 3, as illustrated in FIGS. 2A through 3, to define the irradiation region 13 of radiation emitted from the emitter 10. The collimator 12 is supported by the unshown rotating plate supporting the radiation tube 8 and sensing device 11, and integrally rotates with the radiation tube 8 and sensing device 11 in the same direction at the time of CT imaging.

Radiation generated at the target layer is externally emitted through the target layer and the support substrate holding the target layer. The emission range of the radiation emitted from the emitter 10 is according to that restricted by an unshown forward shield, provided to the emitter 10. The irradiation region 13 is further defined by the collimator 12 provided between the emitter 10 and the accommodation portion 3.

The sensing device 11 is irradiated by the radiation. The collimator 12 restricts the irradiation region 13 so that the entire breast 15 of the subject P is irradiated, all the way to the tip, and so that the transmitted radiation forms a generally square shape on the sensing device 11. The irradiation region 13 is defined by a radiation transmitting portion 12x formed in the collimator 12. When the entire breast 15 is within the irradiation region 13, the radiation which has been transmitted through the breast 15 reaches the sensing device 11, and thus a transmission image of within the breast 15 is obtained. Heavy metals which have radiation shielding properties, such as lead, tungsten, tantalum, rhenium, and so forth, are suitable as materials for the collimator 12.

The term "collimator 12" according to the present invention refers to a member formed of a radiation shielding material which shields part of the radiation emitted from the radiation tube 8 so as to restrict part or all of the perimeter of the irradiation region 13. The collimator 12 is formed in a frame shape in plane view, with the radiation transmitting portion 12x, which is an opening defined by a first defining member 12a, a second defining member 12b, a third defining member 12c, and a fourth defining member 12d, all formed of radiation shielding materials. The collimator 12 is provided separately from the radiation tube 8 and close to the accommodation portion 3, so the penumbra, which readily occurs in arrangements where the radiation tube 8 and collimator are integral and collimation is performed at a position away from the accommodation portion 3, can be reduced. At the same time, the amount of shift of the irradiation region 13 as to the sensing device 11 due to relative positional shift between the radiation tube 8 and the collimator 12 can be suppressed. The collimator 12 may be formed so to have a cross-sectional shape in the form of the letter "U", or the equals symbol "=", which will be described later.

Shield

A plate-shaped shield 14 is provided on the inner side of the front face plate 7 of the gantry 2, surrounding the perimeter of the insertion opening 17, as illustrated in FIGS. 2A through 3. The shield 14 is provided to isolate the irradiation region 13 and the subject P from each other, and follows the front face plate 7 between insertion opening 17 and the rotation path of the emitter 10 created by rotation of the radiation tube 8. The shield 14 has an annular shape, with the middle portion corresponding to the insertion opening 17 and the accommodation portion 3 leading thereto being open. The shield 14 is to shield the subject P from direct irradiation by radiation from the radiation tube 8, scattered radiation occurring when radiation strikes the collimator 12, and so forth, thus preventing radiation from leaking to the subject P. Heavy metals which have high radiation shielding properties, such as lead, tungsten, tantalum, rhenium, and so forth, are suitable as materials for the shield 14. While the shield 14 is usually a circular annular shape, an elliptic annular shape, rectangular annular shape, or the like, may be employed.

The shield 14 is preferably situated on the inner face of the front face plate 7, at least closer to the rotation path of the emitter 10 than the rotation path of the collimator 12. The shield 14 also preferably covers the entire inner face of the front face plate 7 between the insertion opening 17 and the rotation path of the emitter 10 according to rotation of the radiation tube 8. Disposing the shield 14 on the inner face of the front face plate 7 enables irradiation of the subject P by excessive radiation to be prevented. Specifically, radiation directly irradiated to the subject P from the radiation tube 8, and leakage of scattered radiation generated by the collimator 12 being irradiated by radiation, can be prevented.

Imaging System

Figure 4:
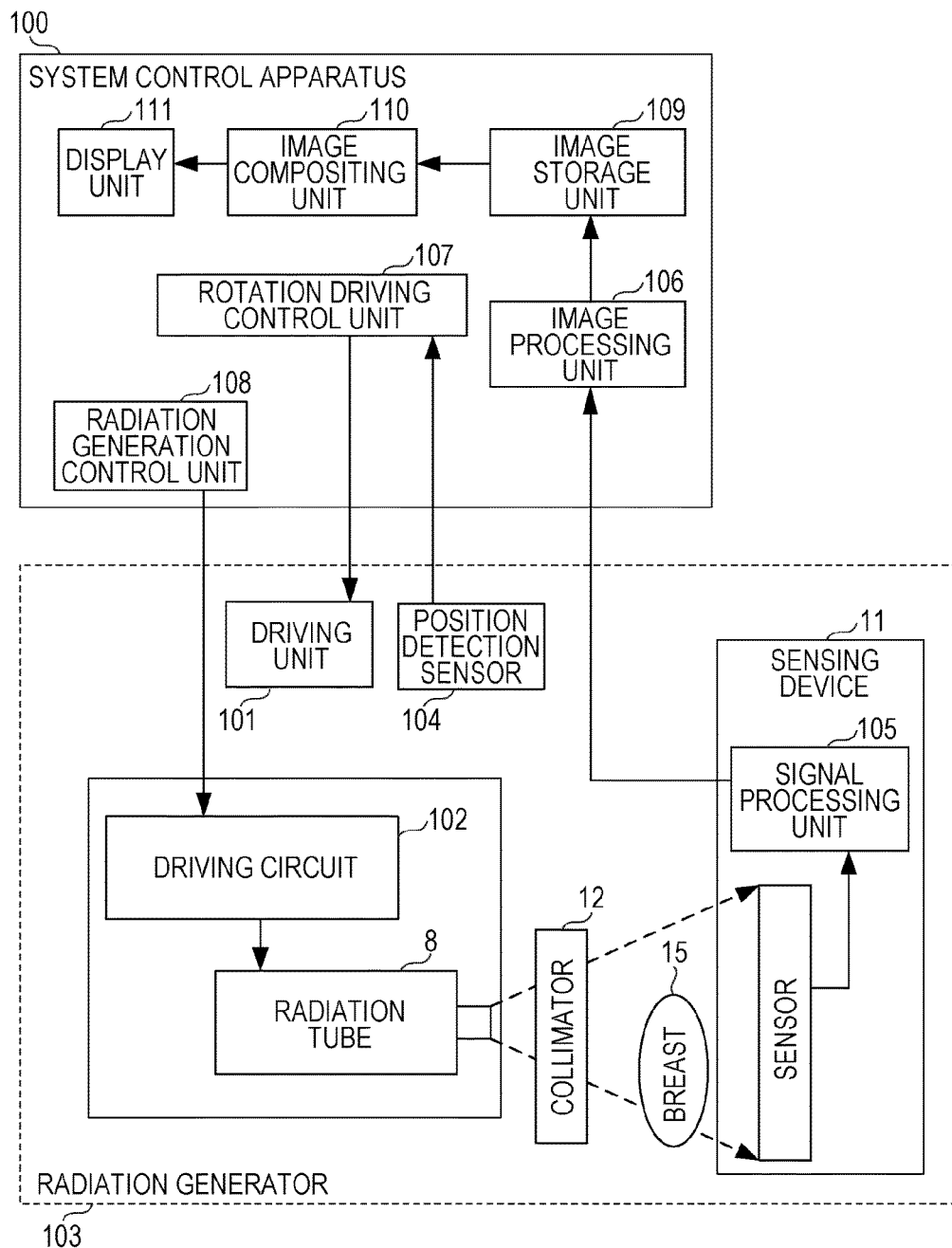
FIG. 4 is a configuration diagram of a mammographic CT apparatus imaging system according to the present invention.

FIG. 4 is a configuration diagram illustrating the mammographic CT system according to the present invention. A system control apparatus 100 controls a radiation generator 103 including the radiation tube 8 and a driving circuit 102 thereof, the sensing device 11, and the driving unit 101. The driving circuit 102 outputs various types of control signals to the radiation tube 8 under control of a radiation generation control unit 108 of the system control apparatus 100. The rotation driving control circuit 107 outputs driving control signals to the driving unit 101, based on position information from a position detection sensor 104 for detection the rotational position of the rotating plate supporting the radiation tube 8 and other components, under control of the system control apparatus 100. The emission state of radiation emitted from the radiation generator 103 is controlled while rotating the driving unit 101 a predetermined amount by the driving control signals. Radiation emitted from the radiation generator 103 is partially shielded by the collimator 12 and the like, passes through the breast 15, and is sensed at the sensing device 11. The sensing device 11 converts the sensed radiation into image signals, and outputs the image signals to a signal processing unit 105. The signal processing unit 105 subjects the image signals to predetermined signals processing under control of the system control apparatus 100, and sends these to an image processing unit 106. The image processing unit 106 of the system control apparatus 100 forms a CT image from the image information imaged at each rotation position, and stores this in an image storage unit 109. The radiation tube 8 and sensing device 11 are rotated once around the breast 15, while multiple CT images are being taken. These images are composited at an image compositing unit 110, thereby generating a three-dimensional image, which is displayed on a screen of a display unit 111.

Second Embodiment

Figure 5A:
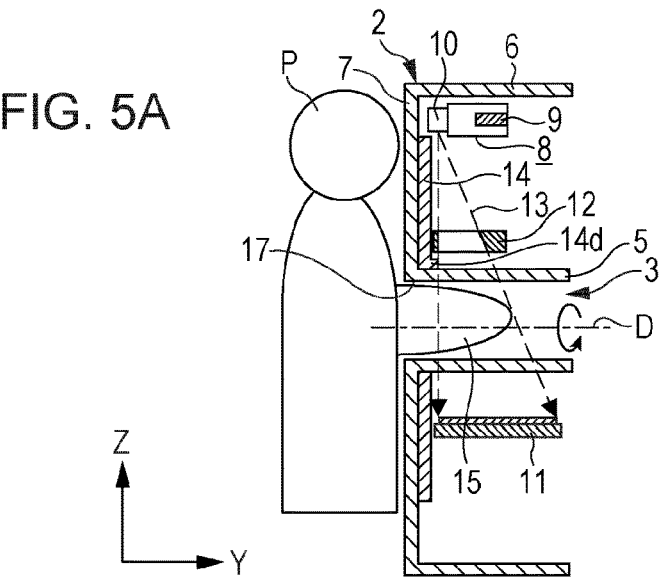
FIG. 5A is a cross-sectional view of a mammographic CT apparatus according to a second embodiment, as viewed from the X direction in FIG. 1.
Figure 5B:
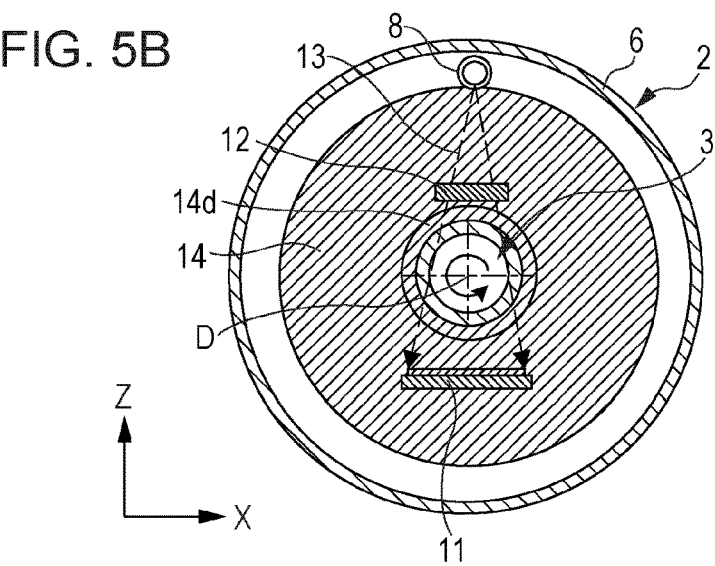
FIG. 5B is a cross-sectional view of the mammographic CT apparatus according to the second embodiment, as viewed from the Y direction in FIG. 1.
Figure 5C:
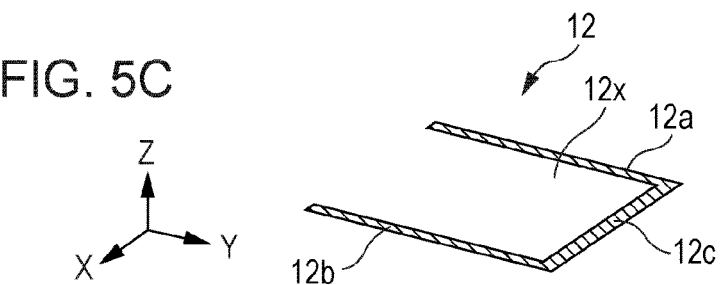
FIG. 5C is an enlarged perspective view of a collimator.
Figure 6:
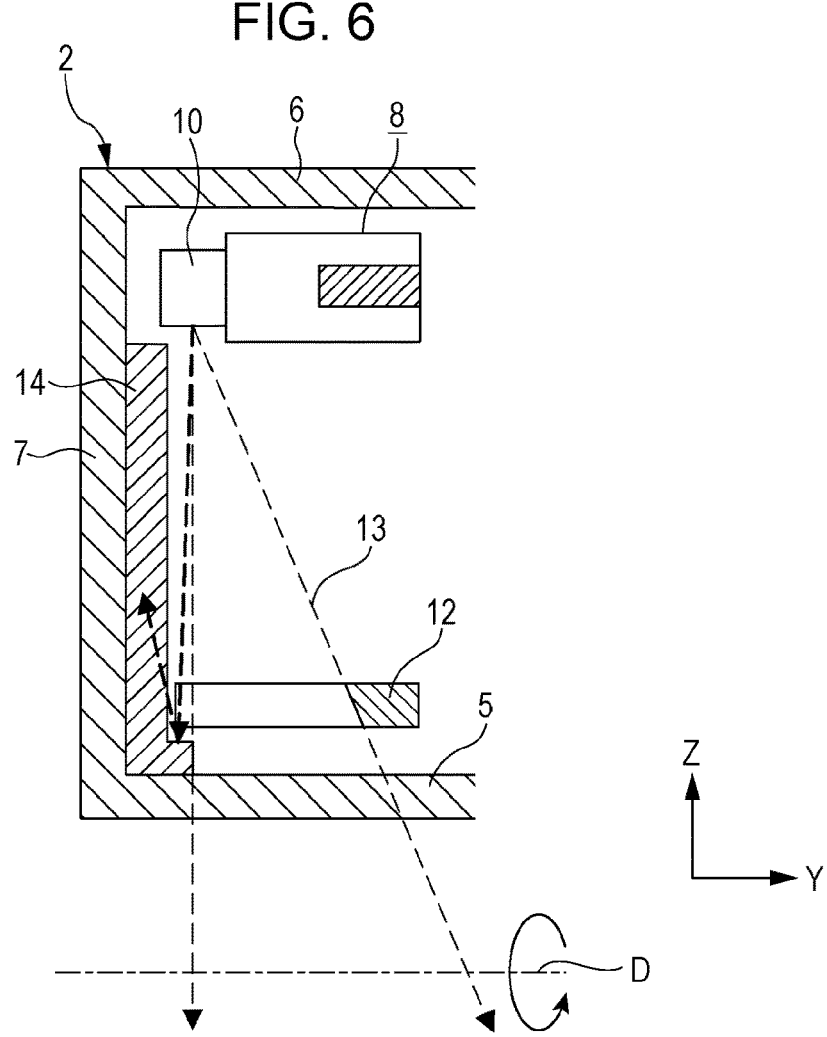
FIG. 6 is an enlarged view of around a collimator according to the second embodiment.

A second embodiment will be described. The mammographic CT apparatus according to the present embodiment differs from that in the first embodiment with regard to the shape of the collimator 12, and whether or not a protrusion 14d is provided to the shield 14, as illustrated in FIGS. 5A through 6. The irradiation region 13 of radiation emitted from the emitter 10 of the radiation tube 8 is defined by the collimator 12 and protrusion 14d in the present embodiment.

To specifically describe the features of the present embodiment, the collimator 12 is an open-box shape in plane view, having the radiation transmitting portion 12x defined by the first defining member 12a, second defining member 12b, and third defining member 12c, with the side of the radiation transmitting portion 12x toward the front face plate 7 open. The collimator 12 has the three sides of the irradiation region 13, other than that toward the front face plate 7, defined by the first defining member 12a, second defining member 12b, and third defining member 12c. The shield 14 is provided covering the entire inner face of the front face plate 7 between the insertion opening 17 and the rotation path of the emitter 10 according to rotation of the radiation tube 8. The annular protrusion 14d is provided on the portion of the shield 14 farther toward the insertion opening 17 than the rotational path of the collimator 12, so that the portion of the irradiation region 13 toward the front face plate 7 side is defined by this protrusion 14d.

Now, a certain gap has to be provided between the collimator 12 and shield 14 in order to move the collimator 12. According to the above-described configuration, the protrusion 14d defines the irradiation region 13 toward the front face plate 7 side, and at the same time prevents radiation from leaking through this gap to the subject P. The collimator 12 has no defining member toward the front face plate 7 side, so a irradiation region 13 can be formed close to the front face plate 7. Accordingly, a wide region can be imaged including around the base of the breast 15.

It is sufficient for the protrusion 14d to be protruding by an amount corresponding to the gap between the first defining member 12a and second defining member 12b and the shield 14. However, it is more preferably for the protrusion 14d to be protruding farther toward the inner side of the gantry 2 than the edge of the collimator 12 facing the front face plate 7, to facilitate shielding of unwanted radiation.

Figure 7:
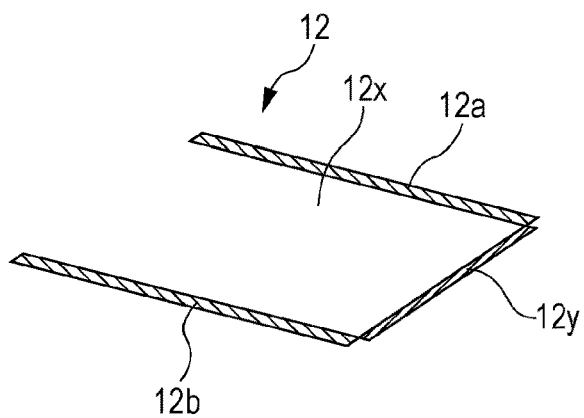
FIG. 7 is perspective view of another example of a collimator.

The collimator 12 to be combined with the protrusion 14d may be that frame-shaped in plane view as described earlier, or that illustrated in FIG. 7. The collimator 12 illustrated in FIG. 7 has the form of an equals symbol "=" in plane view, with the first defining member 12a and second defining member 12b having been linked by a linking member 12y which has no radiation shielding properties. Combining the collimator 12 having a frame shape in plane view with the protrusion 14d enables leakage of radiation from the gap between the collimator 12 and shield 14 to be prevented. Combining the collimator 12 having the form of an equals symbol "=" in plane view with the protrusion 14d yields the same advantage as the combination of the collimator 12 having the form of an open box in plane view and the protruding alone.

Third Embodiment

Figure 8A:
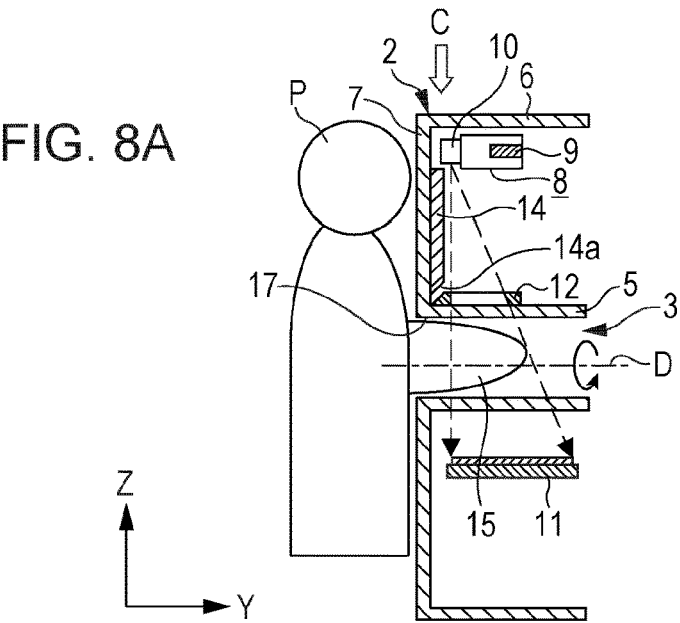
FIG. 8A is a cross-sectional view of a mammographic CT apparatus according to a third embodiment, as viewed from the X direction in FIG. 1.
Figure 8B:
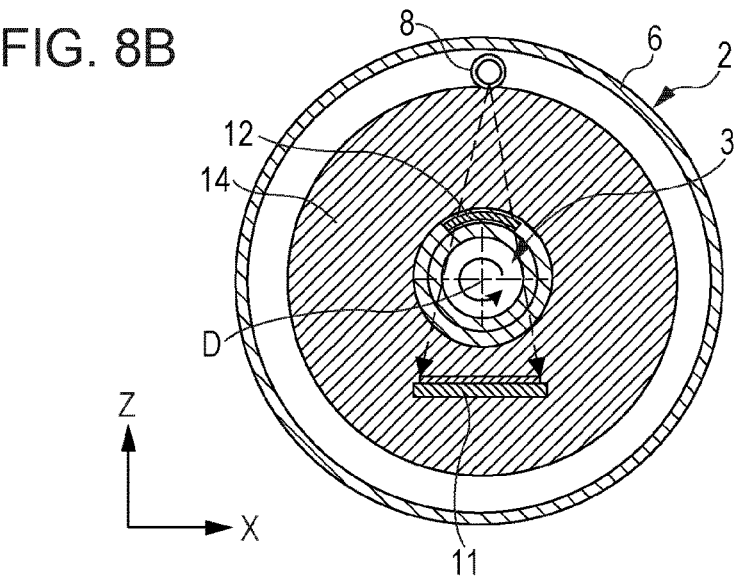
FIG. 8B is a cross-sectional view of the mammographic CT apparatus according to the third embodiment, as viewed from the Y direction in FIG. 1.
Figure 8C:
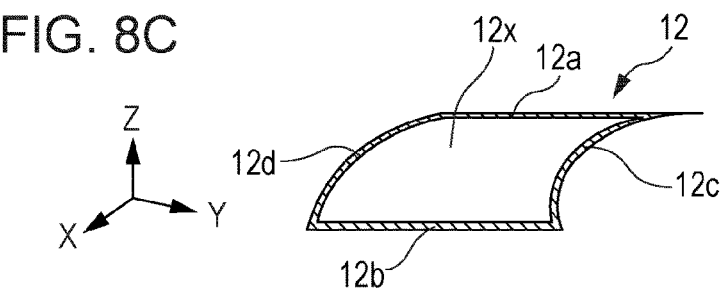
FIG. 8C is an enlarged perspective view of a collimator.
Figure 9:
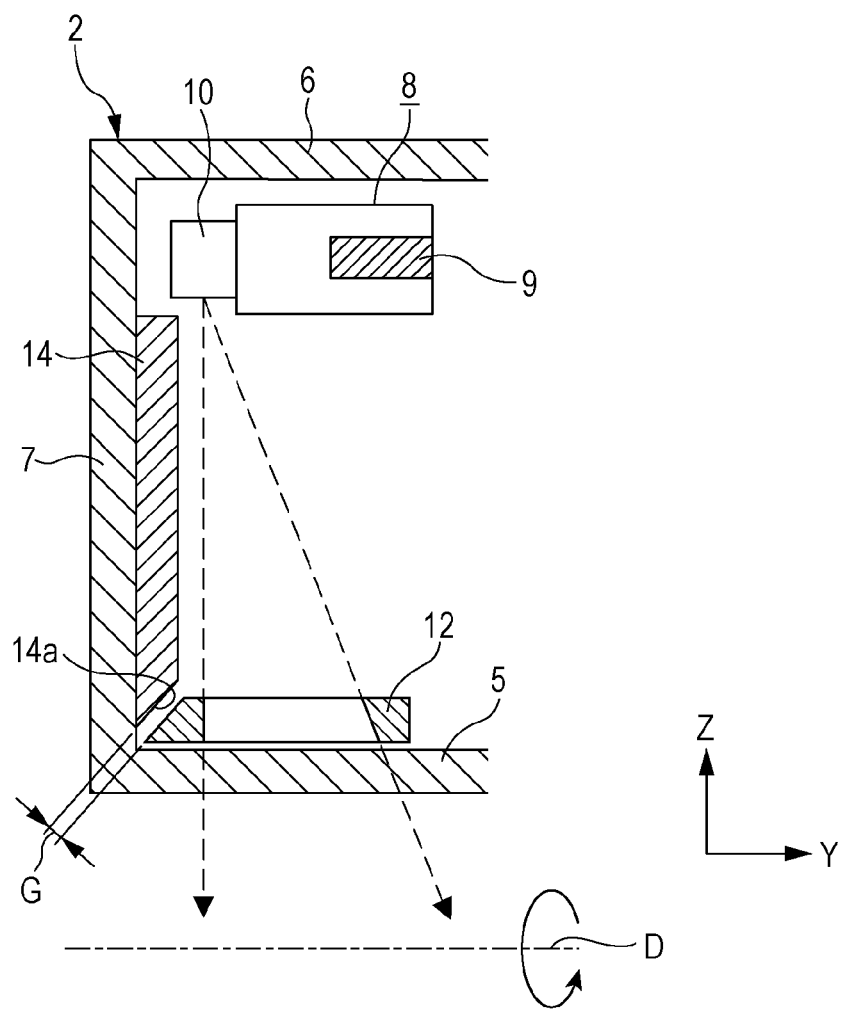
FIG. 9 is an enlarged view of around a collimator according to the third embodiment.

A third embodiment will be described. The mammographic CT apparatus according to the present embodiment differs from that in the first embodiment with regard to the shape of the collimator 12, and the layout relation between the collimator 12 and shield 14, as illustrated in FIGS. 8A through 9.

To specifically describe the features of the present embodiment, the inner peripheral face of the annular shield 14 is a tapered face of which the inner diameter of the shield 14 gradually expands toward the inner side of the gantry 2. On the other hand, the collimator 12 according to the present embodiment is the same with the first embodiment in that the shape is in a frame shape in plane view, but is different in being curved in a convex shape toward the outer side of rotation in the radial direction of rotation on the rotation axis D. That is to say, the fourth defining member 12d is situated at the side of the front face plate 7, the third defining member 12c is situated on the opposite side thereof, and the first defining member 12a and second defining member 12b connect the ends of the fourth defining member 12d and the third defining member 12c. The first defining member 12a and second defining member 12b each are curved in a convex shape toward the outer side of rotation in the radial direction of rotation on the rotation axis D. The outer side face of the fourth defining member 12d, which is the edge face of the collimator 12 facing the front face plate 7, is an inclined face inclined in the same direction as the tapered face of the shield 14, and faces the tapered face of the shield 14.

According to the above configuration, the edge of the collimator 12 facing the front face plate 7 is situated closer in the Y direction to the front face plate 7 than the back face of the shield 14 provided closer to the rotational path of the emitter 10 than the rotational path of the collimator 12, over the entire rotation path of the collimator 12. That is to say, even in a case where the collimator 12 is disposed in contact with the shield 14, the collimator 12 can be disposed closer to the front face plate 7 by a distance up to the equivalent of the thickness of the shield 14, so the radiation transmitting portion 12x can be brought closer to the front face plate 7. Accordingly, the irradiation region 13 can be made to extend to the base portion of the breast 15 of the subject P, thus enabling radiography of the base portion of the breast 15. This also facilitates prevention of leakage of scattered radiation, which is generated when restricting the radiation by the collimator 12, to the subject P side. In particular, an arrangement where the tapered face of the shield 14 and the inclined face of the collimator 12 face each other is preferable, since the edge of the collimator 12 can be is situated closer in the Y direction to the front face plate 7 than the back face of the shield 14 without exposing the inner face of the front face plate 7, thereby facilitating prevention of radiation leakage. Further, the center of curvature of the collimator 12 preferably matches the rotation axis D, which facilitates maximal proximity of the tapered face of the shield 14 and the inclined face of the collimator 12.

While the edge of the collimator 12 facing the front face plate 7 is situated further toward the front face plate 7 than the back face of the shield 14 in the Y direction, over the entire the rotation path of the collimator 12, the present invention is not restricted thusly. It is sufficient for the edge of the collimator 12 toward the front face plate 7 to be at least situated closer in the Y direction to the front face plate 7 than the back face of the shield 14. For example, in a case where the collimator 12, radiation tube 8, and sensing device 11 have a rotation path for preliminary rotation other than the exposure period, the above-described arrangement does not necessarily have to be made for the preliminary rotation path.

According to the present invention, a collimator which rotates at the same angular speed as the radiation tube is provided near the accommodation portion, so the irradiation region can be defined at a position near to the sensing device. Accordingly, the region where the penumbra occurs can be narrowed, and the amount of shift of the irradiation region as to the sensing device, due to relative positional shift of the radiation tube and the collimator, can be suppressed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-239626, filed Nov. 20, 2013, which is hereby incorporated by reference herein in its entirety.

REFERENCE SIGNS LIST

1 Mammographic CT apparatus
2 Gantry
3 Accommodation portion
7 Front face plate
8 Radiation tube
11 Sensing device
12 Collimator
14 Shield
15 Breast
101 Driving unit
P Subject
D Rotation axis

The invention claimed is:
1. A Computed Tomography apparatus for breast comprising:
  a gantry, including a front face plate provided with an insertion opening and an accommodation portion into which a breast is inserted through the insertion opening;
  an X-ray tube disposed within the gantry and configured to rotate around a rotation axis
  a sensing device disposed within the gantry and configured to rotate around the rotation axis so as to face the X-ray tube and detect X-rays emitted from the X-ray tube and transmitted through the accommodation portion;
  a driving unit configured to rotate the X-ray tube and the sensing device around the rotation axis at the same angular speed and same direction;
  a collimator having an aperture and configured to collimate the X-rays emitted from the X-ray tube, form an irradiation field and rotate around the rotation axis synchronously with the X-ray tube and sensing device; and
  a shield surrounding a perimeter of the insertion opening is provided on an internal face of the front face plate,
  wherein the shield includes a tapered face of which an inner diameter of the shield gradually expands internally in the gantry and the collimator includes a counter tapered face facing the tapered face.

2. The Computed Tomography apparatus according to claim 1, wherein an edge of the counter tapered face of the collimator is situated closer to the front face plate than a back side end of the shield.

3. The Computed Tomography apparatus according to claim 2, wherein the edge of the counter tapered face of the collimator is situated closer to the front face plate than the back side end of the shield, over an entire rotational path of the collimator.

4. The Computed Tomography apparatus according to claim 1, wherein the tapered face is inclined such that an inner diameter of the shield gradually expands toward the inner side of the gantry, the collimator is curved in a convex shape toward the outer side of rotation in the radial direction.

5. The Computed Tomography apparatus according to claim 4, wherein the center of curvature of the collimator matches the rotation axis.

6. The Computed Tomography apparatus according to claim 1, wherein a front side the collimator is open.

7. The Computed Tomography apparatus according to claim 1, wherein the shield has an internal protruding portion protruding internally in the gantry, and
wherein the shield overlaps the collimator along the rotation axis.

8. The Computed Tomography apparatus according to claim 1, wherein the shield is located between the front face plate and the collimator in the rotation axis.

9. The Computed Tomography apparatus according to claim 1, wherein the shield overlaps the collimator in a radial direction of the gantry.

10. A Computed Tomography apparatus for breast comprising:
a gantry including a front face plate provided with an insertion opening and an accommodation portion into which a breast is inserted through the insertion opening;
an X-ray tube disposed within the gantry and configured to rotate around a rotation axis;
a sensing device disposed within the gantry and configured to rotate around the rotation axis so as to face the X-ray tube and detect X-rays emitted from the X-ray tube and transmitted through the accommodation portion;
a driving unit configured to rotate the X-ray tube and the sensing device around the rotation axis at the same angular speed and same direction; and
a collimator having an aperture and configured to collimate the X-rays emitted from the X-ray tub, form an irradiation field and rotate around the rotation axis synchronously with the X-ray tube and sensing device;
a shield surrounding a perimeter of the insertion opening is provided on an internal face of the front face plate,
wherein the shield has an internal protruding portion protruding internally in the gantry, and
wherein the shield overlaps the collimator along the rotation axis.

11. The Computed Tomography apparatus according to claim 10, wherein the internal protruding portion is located closer to the insertion opening than the collimator.

12. The Computed Tomography apparatus according to claim 10, wherein the internal protruding portion is located annularly around the rotation axis.

13. The Computed Tomography apparatus according to claim 10, wherein a front side of the collimator is open.

14. The Computed Tomography apparatus according to claim 10, wherein the shield is located between the front face plate and the collimator in the rotation axis.

15. The Computed Tomography apparatus according to claim 10, wherein the shield overlaps the collimator in a radial direction of the gantry.

\* \* \* \* \*